(12) United States Patent
Islava

(10) Patent No.: US 11,311,694 B2
(45) Date of Patent: Apr. 26, 2022

(54) QUICK ADJUST MASK AND METHOD FOR USING THE SAME

(71) Applicant: Steve Islava, Newport Beach, CA (US)

(72) Inventor: Steve Islava, Newport Beach, CA (US)

( * ) Notice: Subject to any disclaimer, the term of this patent is extended or adjusted under 35 U.S.C. 154(b) by 338 days.

(21) Appl. No.: 16/405,077

(22) Filed: May 7, 2019

(65) Prior Publication Data

US 2019/0351171 A1 Nov. 21, 2019

Related U.S. Application Data

(60) Provisional application No. 62/671,530, filed on May 15, 2018.

(51) Int. Cl.
*A61M 16/06* (2006.01)

(52) U.S. Cl.
CPC .... *A61M 16/0683* (2013.01); *A61M 16/0644* (2014.02)

(58) Field of Classification Search
CPC ........... A61M 16/06–0694; A61M 2016/0661; A61M 18/02; A61M 18/025; A62B 23/02; A62B 23/025; A41D 13/1161–1176
See application file for complete search history.

(56) References Cited

U.S. PATENT DOCUMENTS

| | | | | |
|---|---|---|---|---|
| 2004/0025883 A1* | 2/2004 | Eaton | ................ | A61M 16/0638 128/206.27 |
| 2004/0083534 A1* | 5/2004 | Ruiz | ................. | A61M 16/0683 2/171.2 |
| 2004/0112384 A1* | 6/2004 | Lithgow | ............ | A61M 16/0611 128/206.21 |
| 2005/0155604 A1* | 7/2005 | Ging | ................. | A61M 16/0875 128/206.21 |
| 2006/0278233 A1* | 12/2006 | McAuley | .......... | A61M 16/0066 128/206.12 |
| 2008/0066761 A1* | 3/2008 | Hodos | ............... | A61M 16/0655 128/206.28 |
| 2011/0259337 A1* | 10/2011 | Hitchcock | ......... | A61M 16/0875 128/207.11 |
| 2013/0306077 A1* | 11/2013 | Greenberg | ........ | A61M 16/0605 128/206.28 |
| 2018/0304036 A1* | 10/2018 | Huang | .............. | A61M 16/0683 |

* cited by examiner

*Primary Examiner* — Valerie L Woodward
(74) *Attorney, Agent, or Firm* — Marcus C. Dawes

(57) ABSTRACT

An apparatus for supplying a patient with oxygen in emergency and/or in conjunction with CPAP devices. The apparatus includes a face mask connected to a number of quick pull adjustment devices that adjust the top and bottom of the face mask, respectively. After being slid over the head of a patient, a paramedic or other user pulls a top strap followed by a bottom strap. No further adjustment is needed in order to form a tight and secure fit on the patient between the face mask and the nose and mouth region of the patient's face. During use, a CPAP inlet or tubing, resuscitation bag, or other means for delivering oxygen is connected to an inlet of the face mask. The face mask is removed from the patient by manipulating each of the quick pull adjustment devices and then pulling the top strap and bottom strap there through.

11 Claims, 4 Drawing Sheets

QUICK ADJUST MASK AND METHOD FOR USING THE SAME

RELATED APPLICATIONS

The present application is a non-provisional application of U.S. application Ser. No. 62/671,530, filed on May 15, 2018, which is incorporated herein by reference and to which priority is claimed pursuant to 35 USC 120.

BACKGROUND

Field of the Technology

The invention relates to the field of continuous positive airway pressure (CPAP) machines, specifically an adjustable mask for use in conjunction with a CPAP machine.

Description of the Prior Art

CPAP or continuous positive airway pressure machines are a type of ventilator which have long been used to apply a consistent gentle air pressure to the airway of a patient or other individual having trouble breathing. CPAP machines are commonly used by patients who are suffering from congestive heart failure or who are in severe asthmatic respiratory situations which result in acute respiratory distress that prevents the patient from inflating their lungs or taking a deep breath. It is possible to intubate the patient but this can often initiate a gag reflex. Additionally, in many situations a mask with a flow of oxygen may be applied, however while helpful, such a configuration for the patient is often not enough.

A typical CPAP machine consists of a flow generator and a face mask joined together through a flexible hose. The patient places the mask over their nose and mouth so that the positive air flow produced by the generator is directed directly into their airway. The face mask typically comprises at least one strap with a hook and latch fabric which is manipulated about the head and face of the patient so as to maintain the face mask at the proper position over the nose and mouth of the patient.

Similarly, resuscitation or CPR masks are used by emergency personnel such as firefighters and paramedics in treating individuals who are suffering from smoke inhalation or who are otherwise in need of immediate medical treatment. Many resuscitation masks comprise a port or other inlet which allows a resuscitation bag or other treatment device to be coupled to the face mask. Like with a CPAP mask, a resuscitation mask typically comprises at least one strap with a segment of hook and latch fabric which may be placed about the patient, thereby keeping the face mask securely in place over the nose and mouth of the patient.

Both CPAP and resuscitation masks are typically fitted or applied to the face and head of the patient through one or more straps. Some types of straps comprise hook and latch fabric or alternatively, a clip or buckle which couples one end of the strap to an opposing strap end or alternatively to a harness which fits around the back of the patient's head. A problem arises in emergency situations however where time is of the essence and where every second an injured or sick patient is denied oxygen or resuscitation increases the chances of stroke or even death. Specifically, straps with hook and latch fabric can easily get tangled or stuck in the patient's hair or clothing, thereby requiring two rescuers to apply the CPAP apparatus. Additionally, it can be extremely time consuming to try to keep the mask on the patient's face at the proper position while also attempting to attach and detach the hook and latch fabric straps. Furthermore, because the CPAP device cannot be turned on until it is fitted onto the patient, this increases the level of anxiety for the patient and the paramedics as the mask is being placed which in turn increases the likelihood that the paramedic needs to continually readjust the mask, thereby lengthening the time before treatment is initiated. When the CPAP is turned on to apply the oxygen pressure, it can be loud and can further increase the stress level of the paramedics who are already struggling to fit the CPAP on the patient by repeatedly pulling on the hook and latch fabric straps. Additionally, the patient's hair and sweat adds further difficulty and sometimes makes it necessary that more than one health care provider be used to apply this type of head strap. In short, because many prior types of straps or means for fixing the mask to the patient previously used require a certain degree of dexterity by the person putting on the mask, the mask is overall more difficult and time consuming to apply.

What is needed therefore is a means for quickly securing and adjusting the mask about the patient that is simple and easy to use by a single medical professional which ensures that the patient can begin receiving treatment as fast as possible.

BRIEF SUMMARY

The current invention solves the problem of quickly securing a face mask to the face of a patient with a minimal amount of effort on the part of the user or medical professional who is applying the current invention to the patient. The current invention includes a face mask, an adjustable first strap that is removably coupled to the face mask, and an adjustable second strap which is also removably coupled to the face mask. The adjustable first and second straps each comprise tightening means for bringing the face mask against the face of the patient and locking it into position when at least one free end of either the adjustable first or the second strap is pulled in a direction away from the face mask.

In one embodiment, the tightening means of the adjustable first strap of the apparatus includes at least two opposing ends which are threaded through a corresponding strap adjuster. In this embodiment, a removable loop is further coupled to the face mask and disposed through at least one of the strap adjusters.

In another embodiment, the tightening means of the adjustable second strap includes at least two opposing ends of the second adjustable strap which are threaded through a corresponding adjustment hook. Here, each adjustment hook specifically includes a hook which is configured to interact with an aperture that is disposed on the face mask.

In yet another embodiment, the device also includes an adjustable forehead pad.

The current invention also provides an apparatus for quickly applying a face mask to a patient. The apparatus principally includes a face mask and an adjustable harness which is removably attached to the face mask. The harness itself includes a plurality of tightening means for bringing the face mask against the face of the patient which also lock it into position when a portion of the harness is pulled in a direction away from the face mask.

The current invention further provides a method for quickly securing a face mask to the face of a patient. The method includes disposing a face mask over the face of the patient while simultaneously disposing a harness that is removably coupled to the face mask over the back of the patient's head. Next, at least one free end of a strap of the harness is pulled in a direction away from the face mask. By pulling the at least one free end of the strap, the face mask is brought against the face of the patient without any further physical manipulation on the part of the user.

In one embodiment, pulling at least one free end of a strap of the harness in a direction away from the face mask includes either pulling at least one free end of an upper strap of the harness in a direction away from the face mask, or pulling at least one free end of a lower strap of the harness in a direction away from the face mask. When the at least one free end of the upper strap of the harness is pulled in a direction away from the face mask, the at least one free end of the strap is also pulled through a strap adjuster coupled to the face mask. Conversely, when pulling at least one free end of the lower strap of the harness in a direction away from the face mask, the at least one free end of the strap is also pulled through an adjustment hook coupled to the face mask.

In another embodiment, pulling at least one free end of a strap of the harness in a direction away from the face mask includes pulling at least two free ends of the strap of the harness in two opposing directions, wherein each opposing direction is orientated away from the face mask.

In yet another embodiment, pulling at least one free end of the strap of the harness in a direction away from the face mask also involves tightening a forehead pad against the forehead of the patient.

In a further embodiment, the method also includes attaching the strap of the harness to the face mask. Specifically, attaching the strap of the harness to the face mask includes attaching an adjustment hook to the face mask when the strap is threaded through the adjustment hook. In a related embodiment, attaching the strap of the harness to the face mask specifically attaching a detachable loop to a portion of the face mask and then attaching a tightening means to the detachable loop. The tightening means in this embodiment accommodate the strap of the harness.

In another embodiment, the method also includes manipulating a tightening means which accommodate the strap of the harness. Next, the strap of the harness is pulled in order to bring the at least one free end of the strap closer to the tightening means. The face mask and the harness is then removed from patient's face and head, respectively. In this embodiment, the strap of the harness may be removed or detached from the face mask.

In yet a further embodiment, the method includes attaching an oxygen delivering means to an inlet port that is defined in the face mask.

In a further embodiment, the method includes adjusting a position of a forehead pad relative to the face mask.

While the apparatus and method has or will be described for the sake of grammatical fluidity with functional explanations, it is to be expressly understood that the claims, unless expressly formulated under 35 USC 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 USC 112 are to be accorded full statutory equivalents under 35 USC 112. The disclosure can be better visualized by turning now to the following drawings wherein like elements are referenced by like numerals.

The disclosure and its various embodiments can now be better understood by turning to the following detailed description of the preferred embodiments which are presented as illustrated examples of the embodiments defined in the claims. It is expressly understood that the embodiments as defined by the claims may be broader than the illustrated embodiments described below.

DETAILED DESCRIPTION OF THE PREFERRED EMBODIMENTS

The current invention is a head strap for CPAP devices comprising elastic and quick pull adjustment devices that adjust the top and bottom of the CPAP face mask. The current invention is stretched and then slid over the head. Next the paramedic pulls the top straps snug followed by the bottom straps. No further adjustment is needed in order to form a tight and secure fit on the patient. The current invention makes the paramedics' job easier and quickly puts the patient in advanced treatment faster without any fumbling around or extraneous movement. Furthermore, the current device is less intimidating for paramedics who normally work the complicated hook and latch fabric head pieces found in the prior art and thus allows the paramedic to treat more patients and ultimately save more lives.

Figure 1:
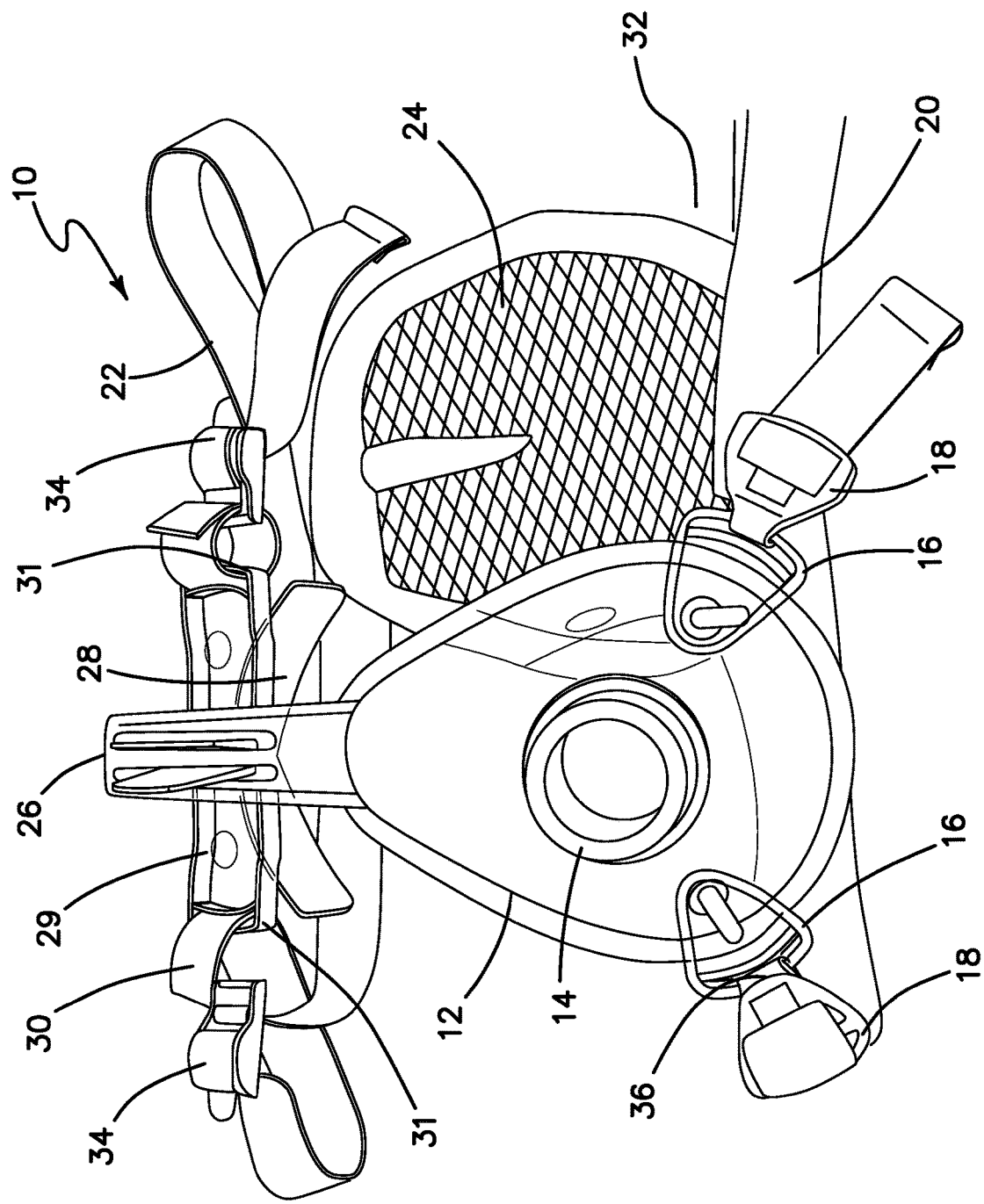
FIG. 1 is a frontal view of the current invention comprising a face mask and a quick adjust harness.
Figure 2:
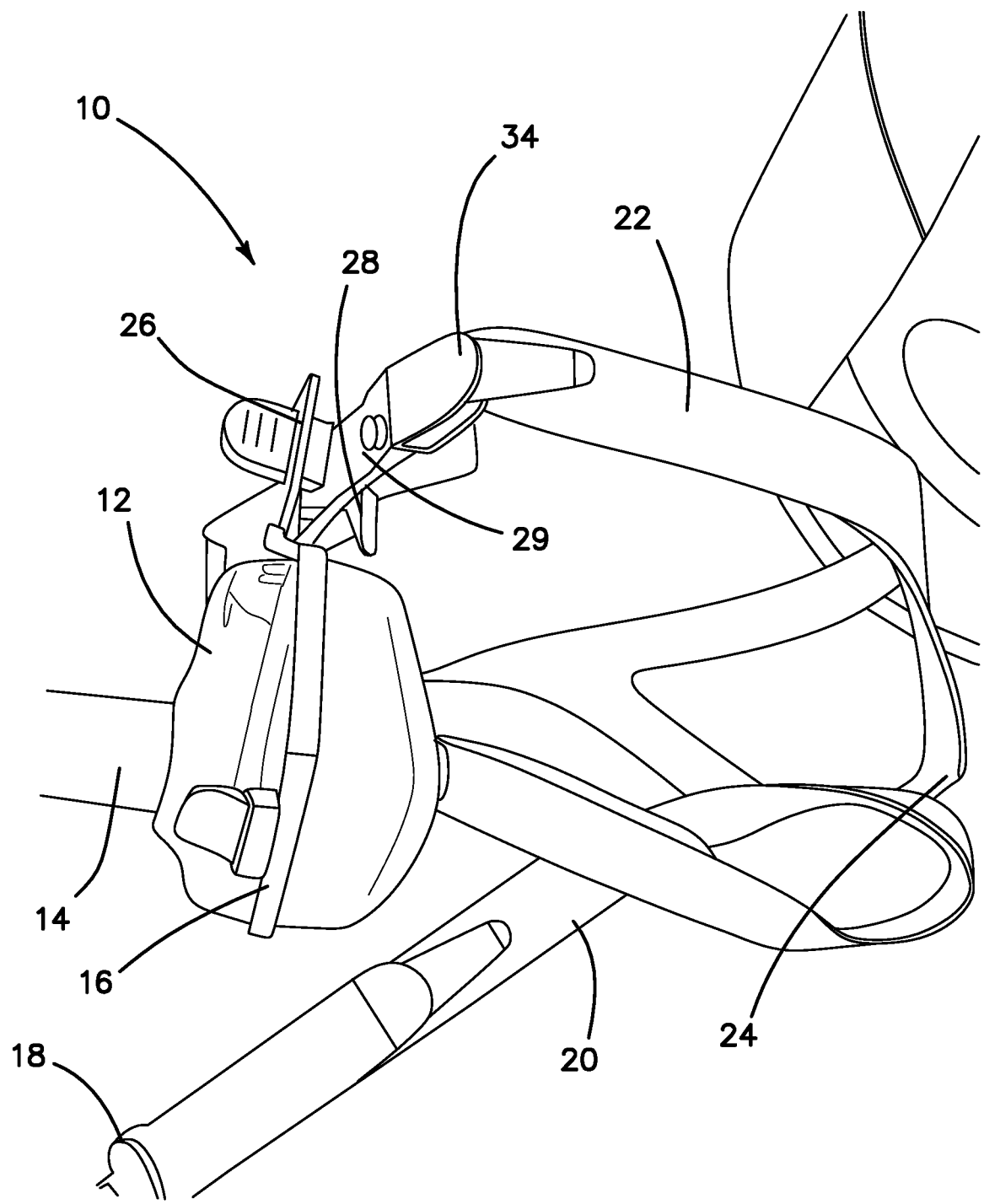
FIG. 2 is a side view of the face mask and harness seen in FIG. 1.

Greater detail of the current invention may be had by turning to FIGS. 1 and 2 where the quick adjust device is denoted generally by reference numeral 10. The quick adjust device 10 principally comprises a face mask 12, a forehead pad 28, and a head harness 32. The face mask 12 is sufficiently sized and shaped to fit over the nose and mouth of a typical patient and further comprises a soft, silicon edge which forms a tight fitting seal with the skin of the patient. In a related embodiment, the face mask 12 may only be sized and shaped to accommodate the nose of the patient, thereby leaving the patient's mouth and oral airway unobstructed. The face mask 12 further comprises an inlet port 14 which is configured to accommodate or couple to a resuscitation bag, flexible tubing, or other structure now known or later devised which is capable of delivering oxygen or other substances to the patient's oral airway. Disposed around the peripheral edge of the face mask 12 is a plurality of links or apertures 16 used to couple the face mask 12 to the head harness 32 as discussed in further detail below. Substantially near the top portion of the face mask 12 is a forehead adjuster 26 which is coupled to the forehead pad 28 and disposed through a crosspiece 29. The forehead pad 28 itself is contoured to accommodate the forehead of the patient as is known in the art. The crosspiece 29 further comprises a link or aperture 31 at either lateral end which are used to further couple the face mask 12 to the head harness 32.

The head harness 32 comprises a soft net 24 which fits around and accommodates the back of the patient's head. Coupled to the upper portion of the net 24 is an upper strap 22 while the lower portion of the net 24 is coupled to a lower strap 20. Both the upper and lower straps 22, 20 are preferably comprised of one or more stretchable or elastic fabrics, however other materials such as nylon, leather, cotton, or polyester may be used without departing from the original spirit and scope of the invention. The lower strap 20 comprises two opposing ends, each end itself comprising an adjustment hook 18. The lower strap 20 is threaded or otherwise disposed through and adjustably coupled to the adjustment hook 18. The adjustment hook 18 itself comprises a hook 36 which is configured to couple or latch onto the apertures 16 of the face mask 12, with each opposing end of the lower strap 20 being coupled to the opposing apertures 16 as seen in FIG. 1. Similarly, the opposing ends of the upper strap 22 are threaded through and adjustably coupled to a strap adjuster 34. Also coupled to each strap adjuster 22 is a loop 30 which is threaded through both each respective strap adjuster 34 and the aperture 31 disposed on either lateral edge of the crosspiece 29. Each loop 30 is preferably comprised of the same material as the straps 20, 22 themselves and may be permanently formed through a sewn seem or other permanent means, however in an alternative embodiment, each loop 30 may comprise a hook and latch fabric or other adjustable means for forming the specific loop shape seen in FIG. 1.

To use the quick adjust device 10, the user or emergency medical professional approaches the patient and slips the device 10 over the patient's head by guiding the patient's head between the face mask 12 and the net 24 of the head harness 32 with the face mask 12 orientated over the patient's face. The face mask 12 is disposed or placed over the nose and mouth of the patient while the net 24 is substantially disposed or placed directly behind the patient's head. Simultaneously, the lower strap 20 and the upper strap 22 are adjusted about the left and right sides of the patient's face and head. In one embodiment, the lower strap 20 is coupled to the face mask 12 via the apertures 16 and adjustment hooks 18 before the device 10 is applied to the patient. However in an alternative embodiment, the adjustment hooks 18 are left separated or uncoupled from the apertures 16 of the face mask 12 as seen in FIG. 2 while the device 10 is being applied to the patient. After the face mask 12 has been sufficiently placed, each adjustment hook 18 is then coupled to its respective aperture 16 by inserting the hook 36 into the aperture 16 where it can be further adjusted as disclosed below.

With the face mask 12 and net 24 properly placed, the emergency medical technician can quickly adjust the fit of the device 10 so that the face mask 12 is securely and tightly fitted over the nose and mouth of the patient. To adjust the position of the forehead pad 28 relative to the face mask 12, the user may grip the opposing tabs of the forehead adjuster 26 and squeeze, thereby moving the forehead adjuster 26 off of the crosspiece 29. The user may then slide the tabs of the forehead adjuster 26 through a pair of slots defined in the crosspiece 29 which moves the forehead pad 28 in a corresponding direction either closer to or further away from the face mask 14. When the user determines the forehead pad 28 is properly placed over the forehead of the patient, the user lets go of the tabs of the forehead adjuster 26 which brings it back into contact with the crosspiece 29 and locks it into position.

Figure 3:
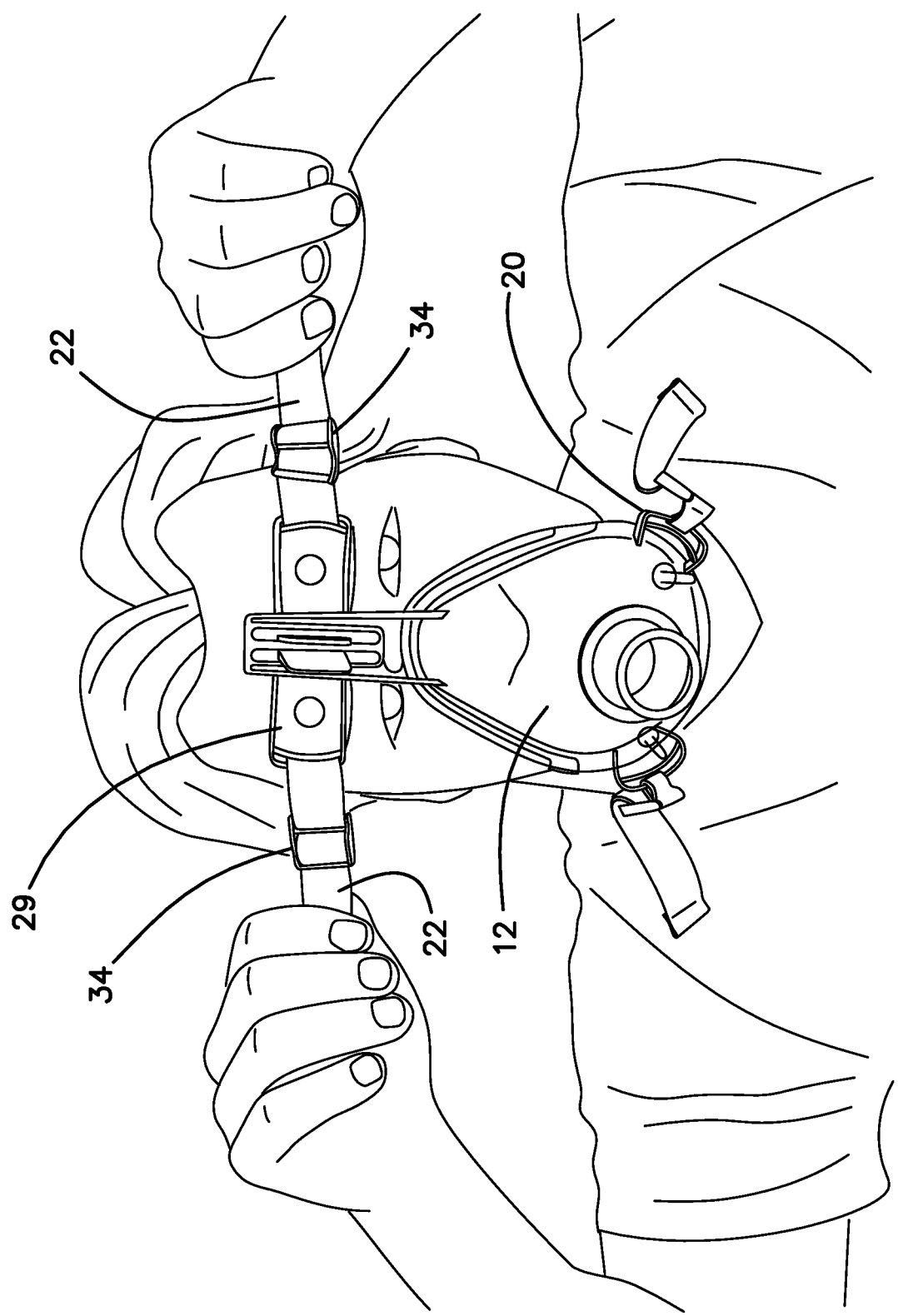
FIG. 3 is a frontal view of the face mask and harness being applied to a patient, specifically with an upper portion of the harness being adjusted to secure the face mask to the patient.
Figure 4:
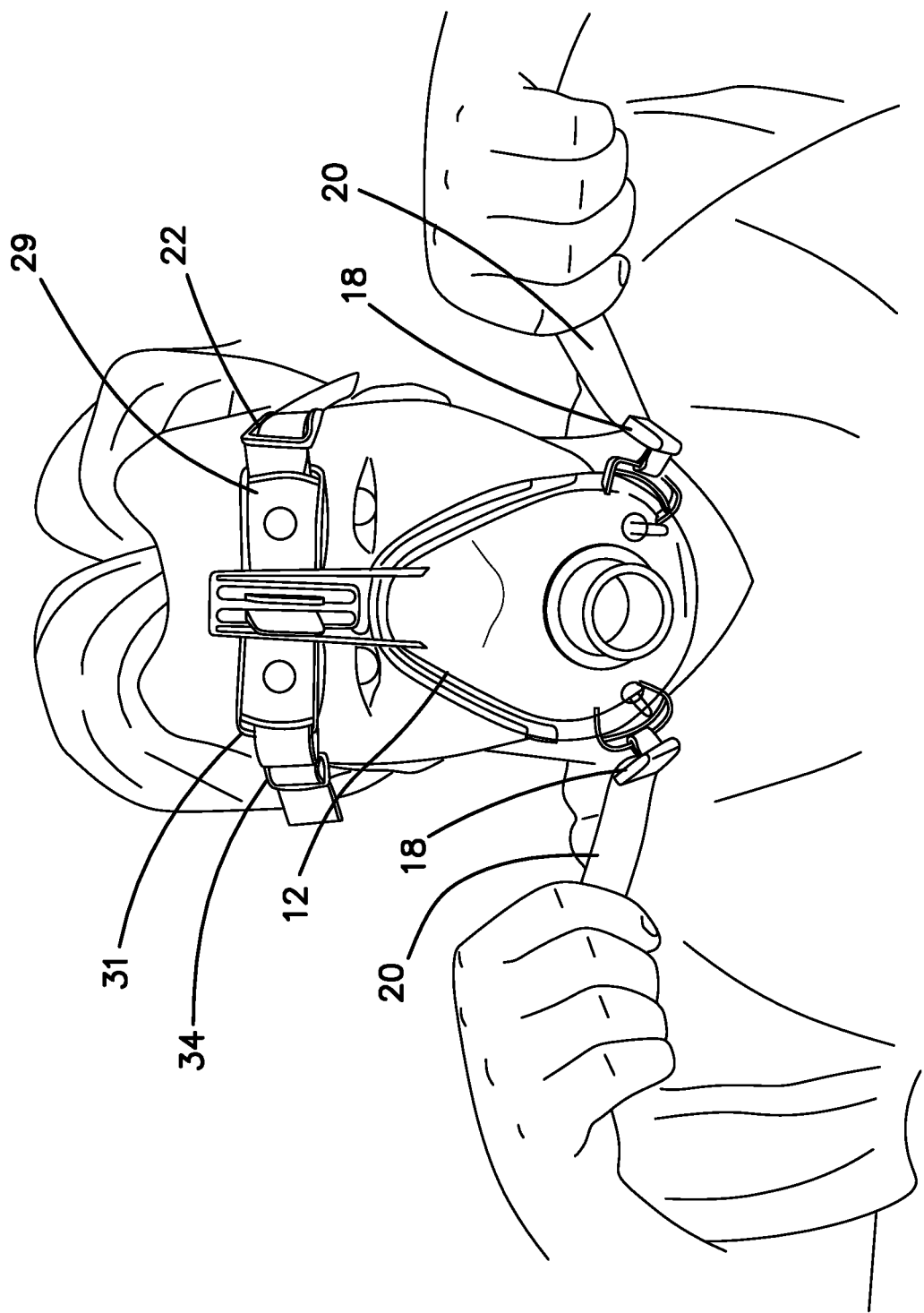
FIG. 4 is a frontal view of the face mask and harness being applied to a patient, specifically with a lower portion of the harness being adjusted to secure the face mask to the patient.

Next, the user/technician firmly grips the opposing loose or free ends of the upper strap 22 which extend beyond the strap adjusters 34 and pulls them in opposing directions away from the face mask 12 as seen in FIG. 3. The pulling of the opposing ends of the upper strap 22 pulls the strap 22 through each respective strap adjuster 34 thereby tightening the upper strap 22 around the patient's head and securely maintaining the forehead pad 28 in position. Next, as seen in FIG. 4, the user firmly grips the opposing free or overhanging ends of the lower strap 20 and pulls it in opposing directions away from the face mask 12, thereby pulling a portion of the lower strap 20 through each respective adjustment hook 18. The pulling of the lower strap 20 effectively tightens the device 10 and brings the face mask 12 into a closer or more secure fit about the nose and mouth of the patient. After pulling the lower strap 20 and the upper strap 22, the device is effectively and efficiently adjusted to the patient's face with a minimum amount of effort or extra steps, thereby reducing the total time required for fitting the device 10 to the patient. Specifically, after the lower strap 20 and the upper strap 22 have been manipulated by being pulled through their respective adjustment hooks 18 and strap adjusters 34, no further action or movement is required by the user, thereby allowing the user to release the free ends of the lower strap 20 and the upper strap 22 and keep the face mask 14 in a secure position without having to perform any other subsequent physical acts such as "locking" or "fixing" the straps 20, 22 into place. In other words, pulling the straps 20, 22 is the only physical act required by the user in order to tightly secure the face mask 14 to the patient's nose and mouth region of their face. After the device 10 has been applied to the patient, either the user or the patient may then attach an oxygen tube, resuscitation bag, or other device to the face mask 14 by inserting the device into the inlet port 14 defined in the face mask 14.

While FIGS. 3 and 4 show a patient placing the device 10 on themselves, it is to be expressly understood that the device 10 may just as quickly and just as easily be placed on a patient by a third party such as an emergency medical technician or other user, even if the patient is in a prone or supine position. In other words, both the upper and lower straps 22, 20 may be manipulated from any orientation, including if the user is standing over, behind, or in front of the patient.

To remove the device 10, both the adjustment hooks 18 and the strap adjusters 34 are manipulated so as to allow the lower strap 20 and the upper strap 22 to be retracted there through, respectively. Specifically, the strap adjusters 34 are manipulated by pulling them forward relative to the upper strap 22, thereby allowing each end of the upper strap 22 to be pulled closer to its respective strap adjuster 34 and increasing the overall length of the upper strap 22. Similarly, each of the adjustment hooks 18 may be pulled forward relative to the lower strap 20 which permits the opposing ends of the lower strap 20 to be pulled closer to each respective adjustment hook 18 and increasing the overall length of the lower strap 20. The retraction of the lower and upper straps 20, 22 through the adjustment hooks 18 and strap adjusters 34 loosens the straps 20, 22, respectively, from about the patient's face and head, allowing the device 10 to be pulled off of or otherwise removed from the patient. Alternatively, the lower strap 20 may be decoupled from the face mask 12 by removing the hook 36 of each adjustment hook 18 from the apertures 16 disposed on the face mask 12, thereby further loosening the device 10 from the patient.

Many alterations and modifications may be made by those having ordinary skill in the art without departing from the spirit and scope of the embodiments. Therefore, it must be understood that the illustrated embodiment has been set forth only for the purposes of example and that it should not be taken as limiting the embodiments as defined by the following embodiments and its various embodiments.

Therefore, it must be understood that the illustrated embodiment has been set forth only for the purposes of example and that it should not be taken as limiting the embodiments as defined by the following claims. For example, notwithstanding the fact that the elements of a claim are set forth below in a certain combination, it must be expressly understood that the embodiments includes other combinations of fewer, more or different elements, which are disclosed in above even when not initially claimed in such combinations. A teaching that two elements are combined in a claimed combination is further to be understood as also allowing for a claimed combination in which the two elements are not combined with each other, but may be used alone or combined in other combinations. The excision of any disclosed element of the embodiments is explicitly contemplated as within the scope of the embodiments.

The words used in this specification to describe the various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself.

The definitions of the words or elements of the following claims are, therefore, defined in this specification to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a subcombination or variation of a subcombination.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptionally equivalent, what can be obviously substituted and also what essentially incorporates the essential idea of the embodiments.

I claim:

1. A method for quickly securing a face mask to a face of a patient comprising:

disposing a face mask over the face of the patient while simultaneously disposing a harness removably coupled to the face mask over the back of the patient's head;

adjusting a vertical position of a crosspiece relative to the face mask while maintaining a horizontal position of the crosspiece relative to the face mask stationary;

pulling at least one free end of a first strap of the harness in a direction away from the face mask, wherein pulling the at least one free end of the strap of the harness in a direction away from the face mask comprises pulling the at least one free end of the strap through a strap adjuster which is directly coupled to at least one removable loop which is in turn coupled to the crosspiece.

2. The method of claim 1 further comprising pulling at least one free end of a second strap of the harness in a direction away from the face mask.

3. The method of claim 2 further comprising coupling the second strap of the harness to the face mask.

4. The method of claim 3 wherein coupling the second strap of the harness to the face mask comprises coupling an adjustment hook to the face mask, wherein the second strap is threaded through the adjustment hook.

5. The method of claim 2 wherein pulling at least one free end of the second strap of the harness in a direction away from the face mask comprises pulling the at least one free end of the second strap through an adjustment hook coupled to the face mask.

6. The method of claim 1 wherein pulling at least one free end of the first strap of the harness in a direction away from the face mask comprises pulling at least two free ends of the strap of the harness in two opposing directions, wherein each opposing direction is orientated away from the face mask.

7. The method of claim 1 wherein pulling at least one free end of the first strap of the harness in a direction away from the face mask comprises tightening a forehead pad coupled to the crosspiece against the forehead of the patient.

8. The method of claim 1 further comprising:

manipulating the strap adjuster accommodating the first strap of the harness;

pulling the first strap of the harness to bring the at least one free end of the strap closer to the strap adjuster; and removing the face mask and the harness from patient's face and head, respectively.

9. The method of claim 8 further comprising uncoupling the first strap of the harness from the face mask.

10. The method of claim 1 further comprising coupling an oxygen delivering means to an inlet port defined in the face mask.

11. The method of claim 1 further comprising adjusting a position of a forehead pad relative to the face mask.

* * * * *